United States Patent [19]

Inada et al.

[11] Patent Number: 5,130,233
[45] Date of Patent: Jul. 14, 1992

[54] METHOD FOR DETERMINING THE β-SUBUNIT OF HUMAN PROLYL HYDROXYLASE BY RADIOIMMUNOASSAY TO DETECT HEPATIC DISEASE

[75] Inventors: Kazuyoshi Inada, Toyama; Akira Oshima, Wakayama; Yasuo Bai, Osaka; Shinichi Yoshida; Kazushi Iwata, both of Toyama, all of Japan

[73] Assignee: Fuji Yakuhin Kogyo Kabushiki Kaisha, Toyama, Japan

[21] Appl. No.: 458,435

[22] Filed: Dec. 28, 1989

[30] Foreign Application Priority Data

Aug. 16, 1985 [JP] Japan .................. 60-179357

[51] Int. Cl.$^5$ .............................................. C12Q 1/26
[52] U.S. Cl. ........................................ 435/7.1; 435/25; 436/86; 436/518; 436/811; 436/820
[58] Field of Search .................. 435/7; 436/518, 541, 436/542, 804, 811, 820

[56] References Cited

U.S. PATENT DOCUMENTS

| | | | |
|---|---|---|---|
| 4,361,647 | 11/1982 | Remington et al. | 435/7 |
| 4,376,110 | 3/1983 | David et al. | 435/7 |
| 4,514,507 | 4/1985 | Secher | 435/7 |
| 4,575,489 | 3/1986 | Higashide et al. | 548/530 |
| 4,623,621 | 11/1986 | Pestka | 435/7 |
| 4,634,666 | 1/1987 | Engleman et al. | 436/548 |

FOREIGN PATENT DOCUMENTS 0193935 9/1986 European Pat. Off. .
1145199 12/1984 Japan .

OTHER PUBLICATIONS

Mansurova et al., Translation of Chemical Abstract 125495a, vol. 101(15), 1984.
*Methods in Enzymology*, vol. XVIIB, Tabor et al. (ed.), Academic Press, New York, pp. 306-316 (1971).
Mansurova et al., *Chemical Abstracts*, vol. 101(15): 125495a (1984).
Yoshida e al., A Sandwich Immunoassay for Human Prolyl 4–Hydroxylase Using Monoclonal Antibody, *Clin. Chim. Acta:* 160 (1986) 37–46.
Kohler et al., "Continuous Cultures of Fused Cells Secreting Antibody of Predefined Specificity", *Nature*, vol. 256, pp. 495–497 (1975).
Kuutti et al., "Human Prolyl Hydroxylase, Purification, Partial Characterization, and Preparation of Antiserum to the Enzyme", Chem. Abst: 159770m, vol. 83 (1975).

*Primary Examiner*—Sam Rosen
*Attorney, Agent, or Firm*—Birch, Stewart, Kolasch & Birch

[57] ABSTRACT

A method for determining human prolyl hydroxylase by radioimmunoassay according to the sandwich method wherein a monoclonal antibody to human prolyl hydroxylase and polyclonal antibody to human prolyl hydroxylase are used, characterized in that a monoclonal antibody to human prolyl hydroxylase is used as at least one of the antibodies which are to be coated on a solid support and to be labeled with a radioactive element. This method is simple and operable with small amounts of samples and gives exact results. Thus, this method is useful for the diagnosis of hepatic diseases. A monoclonal antibody specific to the β-subunit of human prolyl hydroxylase is used to test for the human prolyl hydroxylase.

2 Claims, 1 Drawing Sheet

METHOD FOR DETERMINING THE β-SUBUNIT OF HUMAN PROLYL HYDROXYLASE BY RADIOIMMUNOASSAY TO DETECT HEPATIC DISEASE

This application is a continuation of Ser. No. 06/896,717, filed on Aug. 15, 1986, now abandoned.

BACKGROUND OF THE INVENTION

1. Field of the Invention

The present invention relates to a new simple method for determining human prolyl hydroxylase, which is useful in the straightforward diagnosis of hepatic diseases. More particularly, the present invention relates to a method for determining human prolyl hydroxylase by radioimmunoassay according to the sandwich method using a specific monoclonal antibody to human prolyl hydroxylase as at least one of the antibodies which are to be coated on a solid phase (support) and to be labeled with a radioactive element.

2. Description of the Prior Art

Among methods known hitherto for determining human prolyl hydroxylase (referred to hereinafter simply as hPH) in human blood is included a method wherein 4-L-proline in protocollagen labeled with $^3H$ is used as a substrate and the resultant $^3H$ labeled water is captured by vacuum distillation and measured for its radioactivity (Hutton et al., Anal. Biochem., 16, 384-394, 1966). Other known methods involve the use of $^{14}C$-proline labeled protocollagen as a substrate followed by the measurement of radioactivity from the resultant 4-hydroxylated $^{14}C$-proline (Juva et al., Anal. Biochem. 15, 77-83, 1966); or the use of (pro-pro-gly)$_5$ or (pro-pro-gly)$_{10}$ as a substrate followed by the capture and measurement of $^{14}CO_2$ released from 2-oxo (1-$^{14}C$)-glutaric acid (Berg et al., J. Biol, Chem., 248, 1175-1182, 1973). Any of these methods, however, has disadvantages of requiring complicated, tremendous operations and time-consuming measurements. Furthermore, a simple measurement of hPH activity in blood does not reflect the true hPH level, because most of the hPH is present in blood in an enzymologically inactivated state.

As an immunoassay is known a radioimmunoassay described by Tuderman et al. in Bur. J. Biochem., 60, 399-405, 1975, wherein a labeled antigen is used, utilizing a competitive reaction between the labeled and unlabeled antigens, and determination of hPH is effected after the subsequent reaction with a second antibody. The antibody employed in this competitive reaction is a rabbit polyclonal antibody to hPH. Thus, immunoassay results in low specificity and shows a sensitivity of 5-10 ng for hPH. Moreover, this method is not simple to operate, e.g. requiring centrifugation steps for the separation of the antigen-antibody complex from unbound antigen, and is therefore not a satisfactory method from a practical point of view.

In the foregoing situations, it is quite difficult to measure the quantity of hPH precisely in a simple manner by measuring the enzymatic activity. Thus, there is a great demand for developing a new method for effectively and precisely determining hPH in a simple manner in place of the conventional methods accompanied with various disadvantages, especially in the field of diagnosis of hepatic diseases.

BRIEF SUMMARY OF THE INVENTION

Accordingly, it is an object of the present invention to provide a method for determining hPH by radioimmunoassay.

It is another object of the present invention to provide a method for determining hPH by radioimmunoassay according to the sandwich technique using a specific monoclonal and/or polyclonal antibody to hPH without accompanying drawbacks as seen in the conventional methods.

It is still another object of the present invention to provide a method for determining hPH by radioimmunoassay according to the sandwich technique with a smaller amount of samples in a simpler operation.

Other objects, features and advantages of the present invention will become apparent as the description proceeds.

DETAILED DESCRIPTION OF THE INVENTION

Figure 1:
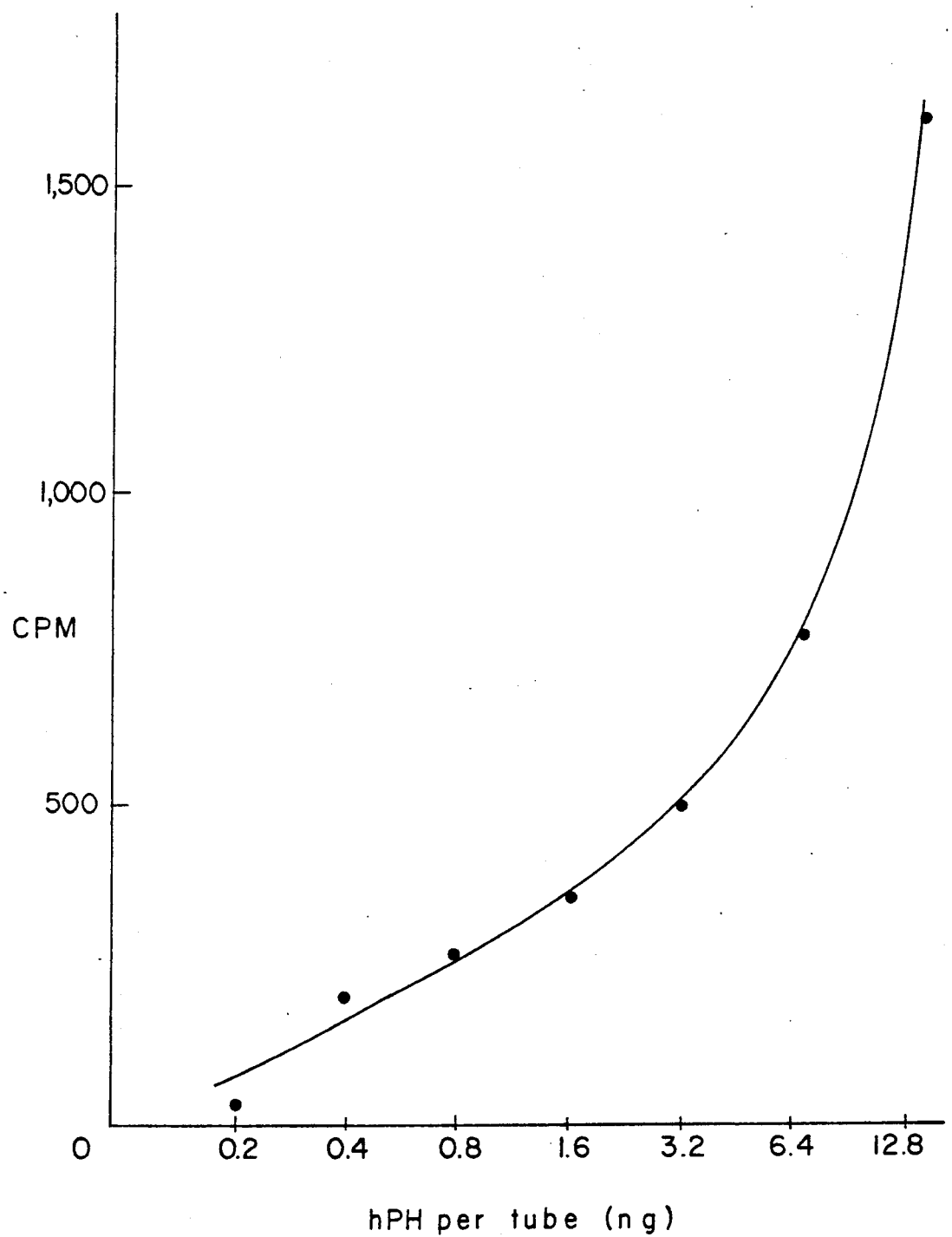
FIG. 1 is a graph showing a hPH standard curve used in the assay in Example 3, which curve was obtained by using a mouse anti-hPH monoclonal antibody coated on polystyrene balls as solid support-coated antibody and using the [$^{125}I$] labeled rabbit anti-hPH polyclonal antibody IgG as labeled antibody in the sandwich method.

As a result of extensive researches made by the present inventors for developing a simple method for determining hPH in a more straightforward and specific manner, it has now been found that a precise and rapid determination of hPH can be carried out with a smaller amount of samples by a method utilizing a radioimmunoassay (RIA) according to the sandwich method using a specific monoclonal and/or polyolonal antibody to hPH.

In accordance with the present invention, there is provided a method for determining hPH by radioimmunoassay wherein a monoclonal antibody to human prolyl hydroxylase and polyclonal antibody to human prolyl hydroxylase are used according to the sandwich method, characterized in that a monoclonal antibody to human prolyl hydroxylase is used as at least one of the antibodies which are to be coated on a solid phase (support) and to be labeled with a radioactive element.

As the antibody to be labeled with a radioactive element in the method of this invention, there is employed an IgG fraction obtainable by fractionation of a material containing antibodies with ammonium sulfate and subsequent purification on a DEAE-cellulose column. In the case where a polyclonal antibody is used, it is preferred to carry out further purification on a 4B affinity column because this would enhance the specificity. It is also possible to use F(ab')$_2$ obtainable by digestion with pepsin. Thus, monoclonal and polyclonal antibodies usable in the method which are of this invention include their specific binding sites F(ab')$_2$ as such.

Labeling of a radioactive element to antibodies can be carried out by known processes for labeling proteins. It is preferred to use [$^{125}I$] as the radioactive nuclide. Labeling with this radioactive nuclide is conveniently carried out by an iodination method with lacto peroxidase. A method described by Thorell et al. in Immunochemistry 11, 203-206 (1974) is used.

The solid support to be coated with the monoclonal or polyclonal antibody should normally be inert to all the substances used for the antigen-antibody reaction including a liquid vehicle and is selected from a wide variety of inorganic and organic inert carrier materials such as glass, caramics and resinous materials in the form of a plate or sphere. Such a solid phase should be homogeneous in quality and identical in size, or otherwise, the quantity of the monoclonal or polyclonal antibody coated on the individual solid phase fluctuates, thus resulting in an inaccurate result of measurements. Because of the easiness in processing, organic resinous materials such as polystyrene, polyvinyl resin, polyamide resin in the form of a plate or sphere a is preferable, with polystyrene balls and polyvinyl chloride plates being most preferable.

In carrying out the method of this invention for determining hPH by radioimmunoassay, a standard solution of hPH and a sample are used and reacted respectively with a solid phase coated with the antibody and thereafter the unreacted materials are removed. After washing, an antibody to hPH which has been labeled with a radioactive element is added to this reaction product to effectuate the reaction.

Unreacted antibody labeled with a radioactive element which does not participate in the reaction is removed and the radioactivity of the labeled antibody bound through hPH is measured. The method itself for the measurement is in accordance with an ordinary method for radioimmunoassay wherein a standard curve is depicted on the basis of the value obtained from the standard solution and the quantity of hPH in the sample is calculated from the standard curve.

Our recent immunological tests have revealed that a significant increase in the hPH levels is observed in tissues or blood of patients suffering from liver fibrosis caused by hepatic diseases such as chronic hepatitis, liver cirrhosis and alcoholic hepatic disorder. As the hPH level in sera from patients with liver cirrhosis measured in accordance with the method of this invention are significantly higher than those of sera from healthy subjects, the measurement of blood hPH levels in a simple manner according to this invention enables foreknowing hepatic diseases, especially liver fibrosis, without relying on biopsy which is burdensome on patients. We have confirmed that fibrosis of hepatic tissues cannot be determined by the conventional liver function tests relying on measurement of the activity of GOT (glutamate-oxaloacetate transaminase), GPT (glutamate-pyruvate transaminase), LDH (lactate dehydrogenase), $\gamma$-GTP ($\gamma$-glutamyl transpeptidase), etc. Thus, the present invention is very useful in the field of diagnosis of hepatic diseases since detection of diseases of this type at an early stage can be expected by the measurement of blood hPH levels according to the method of this invention and since the diagnosis of fibrosis of hepatic tissues can be made by the method of this invention capable of measuring hPH. In addition, the method itself of this invention is simple as compared with the conventional methods and a result obtained by the method of this invention is exact and trustworthy. Thus, the method of this invention is economically advantageous over the conventional methods.

The following examples illustrate the present invention in more detail but are not to be construed as limiting the invention.

EXAMPLE 1

Preparation of anti-hPH monoclonal antibody (a) Preparation of antigen-hPH (EC 1.14.11.2)

Using human placenta as a material, hPH was captured by affinity chromatography on Sepharose 4B coupled with poly-L-proline using CNBr according to the method of Tuderman et al. described in Eur. J. Biochem. 52, 9-16 (1975), and was then purified with a Bio-Gel A-1.5 m (Bio-Rad) column. The hPH sample obtained was examined by electrophoresis with sodium dodecylsulfate-polyacrylamide gel (SDS-PAGE) according to the method of Baum et al. described in J. Virol. 10, 211-219 (1972) whereupon the purity was found to be about 90%.

(b) Preparation of antibody-producing cells

Three Balb/C female mice of 8 weeks old were subjected to a first immunization with the hPH purified in the above (a) in a complete Freund adjuvant. 50 $\mu$g of hPH as a 0.5 ml solution was intraperitoneally administered to each mouse. Further, the mice were subjected to booster immunization with hPH in the same amount dissolved in physiological saline on the 30th and 60th days. As a final immunization, the mice were subjected to subsidiary immunization on the 90th day by intravenous administration (50 $\mu$g/100 $\mu$l physiological saline). After 3 days, spleens of the mice were extirpated and the splenocytes were harvested.

(c) Cell fusion:

The following materials and methods were employed:

RPMI 1640 culture medium: To RPMI No. 1640 (Difco Laboratories) were added sodium bicarbonate (12 mM), sodium pyruvate (1 mM), L-glutamine (2 mM), penicillin G potassium (50 $\mu$/ml), streptomycin sulfate (50 $\mu$g/ml) and amikacin sulfate (100 $\mu$g/ml). The pH was adjusted to 7.2 with dry ice and the mixture was sterilized by filtration with a 0.2 $\mu$m Toyo membrane filter.

NS-1 culture medium: To the above RPMI-1640 culture medium was added a sterile fetal bovine serum (Granite Diagnostic, Inc.) at a concentration of 15% (v/v).

HAT selection medium: The above NS-1 culture medium was further incorporated with hypoxanthine (100 $\mu$M), aminopterine (0.4 $\mu$M) and thymidine (16 $\mu$M).

HT culture medium: The same composition as the HAT selection medium except that the aminopterine had been omitted.

PEG 4000 solution: A 50% (w/w) non-serum solution of the RPMI 1640 culture medium in polyethylene glycol 4000 (PEG 4000, Merck & Co., Inc.) was prepared.

The fusion with 8-azaguanine-resistant myeloma cell lines NS-1 (P3-NS1-1) was carried out by somewhat modifying the method of Oi et al. described in Selected Method in Cellular Immunology (ed. B. B. Mishell and S. M. Shiigi), W. H. Freeman and Company (1980), 351-372. 1.5×10$^8$ karyo-splenocytes (cell viability: 95%) were fused with 2.8×10$^7$ cells of NS-1 myeloma cells (cell viability: 95%). The karyo-splenocytes and myeloma cells were separately washed with the RPMI 1640 culture medium described above. They were suspended in the same culture medium whereby they were mixed in the ratio above described for fusion. Using a 50 ml conical test tube made of styrene resin (Corning Glass Works), the mixture in 40 ml of the RPMI-1640 culture medium was centrifuged for 10 minutes at 400 xg to remove the supernatant completely by suction. To the precipitated cells was added dropwise over one minute under gentle agitation 1 ml of the PEG 4000 solution warmed at 37° C. Further agitation was carried out for one minute to resuspend the cells for dispersion. Next, 1 ml of the RPMI-1640 culture medium warmed at 37° C. was added dropwise in one minute. After repeating this operation once more, 7 ml of the same culture medium was added dropwise over 2-3 minutes under continuous agitation to effect dispersion of the cells. This mixture was subjected to centrifugal separation for 10 minutes at 400 xg and the supernatant was completely removed by suction. To the precipitated cells was added immediately 10 ml of the NS-1 culture medium warmed at 37° C., and large clumps of cells were carefully pipetted with a 10 ml pipette for dispersion. Further, 20 ml of the same culture medium was added to dilute the dispersion, and it was distributed in a 96-well microplate (Corning Glass Works) made of polystyrene so that $5.9 \times 10^5$ cells/0.1 ml of the culture medium may exist in each well. As a preliminary treatment of the 96-well microplate to be used, 0.2 ml of the NS-1 culture medium was added thereto, and the microplate was previously warmed overnight in a carbon dioxide incubator (37° C.) and sucked to remove the culture medium just before use. The microplates where the cell fusion had been finished were incubated at a temperature of 37° C. and a humidity of 100% in 7% carbon dioxide/93% air.

(d) Selective multiplication of the hybridoma in the selection medium

On the first day of incubation, 2 drops (about 0.1 ml) of the HAT selection medium were added with a Pasteur pipette. On the 2nd, 3rd, 5th, 8th and 11th days, a half of the culture medium (0.1 ml) was replaced by a fresh HAT selection medium. On the 14th day, the culture medium was replaced by the HT culture medium and the same operation was repeated every 3-4 days. The growth of a satisfactory hybridoma (the fusion rate: 83%) was observed usually in 2-3 weeks. All of the wells where the hybridoma had grown were checked for positive results according to a solid phase-antibody binding test (ELISA) described in the following item (e). 20 cells/288 wells were detected positive. 1 ml of an HT culture medium containing $10^7$ mouse thymocytes as a feeder was added to a 24-wells plate (Corning Glass Works) made of polystyrene, and the whole contents of the 20 positive hybridomas detected were transferred. They were incubated in the same manner as in the above (c) at 37° C. for about one week in the presence of 7% carbon dioxide. During the incubation, 0.5 ml of the supernatant in each well was replaced once or twice by 0.5 ml of a fresh HT culture medium. At the time the hybridoma had well grown, its positivity was reconfirmed by ELISA and each hybridoma was subjected to cloning according to the limiting dilution method described in item (f) below. The residual solution after used for the cloning was transferred to a 25 cm² tissue culture flask (Corning Glass Works) made of polystyrene to prepare a sample for storage under freezing.

(e) Screening of hybridoma capable of secreting the anti-hPH antibody according to the solid phase-antibody binding test (ELISA)

A method somewhat modifying a method of Rennard et al. described in Anal. Biochem. 104, 205-214 (1980) was employed. This method is suitable for the detection of antibodies from a hybridoma. A 96-well microtitration plate (Flow Laboratories, Inc.) was coated with 0.5-1.0 μg of hPH and the others were blocked with 1% bovine serum albumin (BSA). To this was added an aliquot of the supernatant of the hybridoma-grown well, and the incubation was carried out for about one hour at room temperature. A horseradish peroxidase labeled goat anti-mouse IgG (TAGO, Inc.) as a secondary antibody was added and further incubation was carried out for about one hour at room temperature. Next, hydrogen peroxide and o-phenylenediamino as a substrate were added, and the degree of the resultant brown color was evaluated qualitatively with naked eyes or the absorbance at 500 nm was determined with a CORONA double wave micro-plate spectrophotometer (MTP-22, Corona Denki Kabushiki Gaisha).

(f) Cloning

Since there was a possibility of at least 2 kinds of hybridoma being grown in each well, cloning was performed according to the limiting dilution method to obtain monoclonal antibody-producing hybridomas. A cloning culture medium was prepared which contained $10^7$ mouse thymocytes as feeder per ml of the NS-1 culture medium, and was added to 36, 36 and 24 wells of a 96-wellsmicrotitration plate at 5, 1 and 0.5 hybridomas per each well, respectively. On the 5th and 12th days, about 0.1 ml of NS-1 culture medium was added. A satisfactory growth of the hybridoma was observed 14-15 days after the cloning, and ELISA was carried out for the group where the ratio of negative colony-forming wells among whole wells were more than 50%. In case all hybridomas in the tested wells were not positive the number of colonies in the antibody-positive wells was checked and hybridomas from 4-6 wells were selected from the wells wherein one colony existed and again subjected to cloning. Ultimately, 8 clones were obtained.

(g) Multiplication in vitro and in vivo of the monoclonal antibody:

The resultant clone is incubated in the NS-1 culture medium or the like proper culture medium (in vitro multiplication), and a monoclonal antibody can be obtained from the supernatant of the cultivated medium (the concentration of the monoclonal antibody protein: 10-100 μg/ml). In order to obtain the antibody in a larger amount, on the other hand, Pristane, a tumor formation-accelerator (2, 6, 10, 14-tetramethylpentadecane, Aldrich Chemical Company, Inc.), is intraperitoneally administered to the same type animal (Balb/C mouse) as that providing the thymocytes and the splenocytes in a dose of 0.5 ml per mouse. After 1-3 weeks, $1 \times 10^7$ cells of hybridoma are also intraperitoneally administered whereby an ascites having a concentration of 4-7 mg protein/ml of the monoclonal antibody can be obtained in vivo after 1-2 weeks.

(h) The isotype of heavy chain and of light chain of the monoclonal antibody:

Each of the resultant ascites is first bound to a microtitration plate coated with hPH in accordance with the method of ELISA described above. After washing, an isotype-specific rabbit anti-mouse Ig antibody (Zymed Laboratories) is added. After washing, horseradish peroxidase labeled goat anti-rabbit IgG (H+L) antibody was added and was then detected with 2,2'-azino-di (3-ethylbenzothiazoline sulfate-6) as a substrate and hydrogen peroxide. The results are arranged and shown in Table 1. Among the investigated antibodies, four antibodies had immunoglobulin chains r1/k, one antibody r2b/k, two antibodies μ/k and one antibody μ/k.

Furthermore, each of the resultant monoclonal antibodies was checked for cross-reactivity with hPH subunits by the western blotting method described by Towbin et al. in Proc. Natl. Acad. Sci. USA, 76, 4350–4354 (1979). Four out of the 8 resultant monoclonal antibodies reacted with α chain of 64 KD molecular weight and the remaining 4 antibodies with β chain of 60 KD molecular weight (see Table 1; for subunits, see Chen-kiang et al., Proc. Natl. Acad. Sci. USA, 74, 4420–4424, 1977).

TABLE 1

| Clone | Isotype | Chain | Immunocross-reaction with subunit |
|---|---|---|---|
| 2-1C2 | IgG2b | γ2b/κ | α |
| 2-5G8 | IgC1 | γ1/κ | β |
| 2-6G9 | IgA | α/κ | α |
| 2-7F8 | IgA | α/κ | α |
| 3-2B12 | IgG1 | γ1/κ | β |
| 3-3H9 | IgG1 | γ1/κ | β |
| 3-4H2 | IgM | μ/κ | α |
| 3-6H5 | IgG1 | γ1/κ | β |

(i) Purification of monoclonal antibody

Each ascites obtained in the above (g) was fractionated with ammonium sulfate (40% saturation) and with DEAE-Sephacel (Pharmacia) equilibrated with a 40 mM phosphate buffer solution at pH 8.0, containing 0.06M sodium chloride to obtain the IgG class in an unabsorbed fraction therefrom. This IgG class was further subjected to gel filtration with a Sephacryl S-300 Superfine (Pharmacia) column equilibrated with a 50 mM phosphate buffer solution at pH 7.4, containing 0.42M sodium chloride to separate and remove therefrom the fetal bovine serum in the culture medium and in other mouse proteins. The purification of the IgA and IgM classes was made by eluting them by chromatography on a DEAE-Sephacel column with a gradient from 0.06M to 1.0M sodium chloride, respectively. The others were purified under the same conditions as in the case of the IgG classes.

EXAMPLE 2

Preparation of antiserum and anti-hPH polyclonal antibody (a) Immunization

A female rabbit was subjected to first immunization with the hPH isolated and purified from human placenta in the same manner as in Example 1(a), in a complete Freund adjuvant. A mixture of 200 μg of hPH and 1 ml of the adjuvant was subcutaneously administered to the back in 15 positions, after which 200 μg of hPH in the complete Freund adjuvant was subcutaneously administered to the back of the rabbit every 2 weeks over the period of 4 months to effect booster immunization. After each booster immunization, a blood sample was taken to check its antiserum for anti-hPH activity in accordance with the method described by Hutton et al. in Anal. Biochem. 16, 384–394 (1966). There was exhibited 56% inhibition of the activity with 4 μl of the antiserum. This antiserum was judged to be specific to the hPH from the fact that it formed only one precipitation line when subjected to the Ouchterlony immunodiffusion and immunoelectrophoresis.

(b) Purification of antiserum

The rabbit antiserum obtained in the above (a) was fractionated with sodium sulfate (18% saturation) and then applied to a DEAE-cellulose (DE52, Whatman) column equilibrated with a 17.5 mM phosphate buffer solution at pH 6.3, to obtain anti-hPH polyclonal antibody in unabsorbed fractions (purified IgG fractions).

EXAMPLE 3

Radioimmunoassay according to the sandwich method for hPH (a) Procedure for the preparation of radioactive element-labeled antibody 100 μg of the rabbit anti-hPH IgG obtained in Example 2(b) above was labeled with 1 mCi of Na [$^{125}$I] according to the lactoparoxidase method.

Using a Sephadex G-50 ($\phi$ 1.0×15 cm) column, unbound [$^{125}$I$^-$] was removed. The labeled antibody eluted from the column by using a phosphate buffer solution (pH 7.0) was diluted with a 1% BSA-containing phosphate buffer solution of pH 7.0 for storage (radioactivity 2.4 μCi/μg).

(b) Procedure for the preparation of a solid phase

Mouse hPH monoclonal antibodies were each dissolved in a 0.1M phosphate buffer solution of pH 7.5 containing 0.1% sodium azide and each concentration was adjusted to 0.1 mg/ml. Polystyrene balls (6.5 mm $\phi$) were soaked at 4° C. for 24 hours in the solution to coat the balls with the antibodies. After removal of the antibody solutions used for the soaking, a phosphate buffer solution (pH 7.0) containing 2% BSA was added and the mixtures were shaken at 30° C. for 2 hours. The polystyrene balls were washed with Buffer A (10 mM of a phosphate buffer solution of pH 7.0, containing 0.1% BSA, 0.1M sodium chloride and 0.1% sodium azide) and stored at 4° C. while being dipped in Buffer A.

(c) Assay procedure

An example wherein the polystyrene balls coupled with the monoclonal antibody from the clone number 3-2B12 prepared in the above (b) were used: To test tubes (8$\phi$×75 mm, 8 tubes in duplicate) were added individually the purified standard hPH preparation having concentrations of 0, 0.2, 0.4, . . . 6.4, 12.8 ng/150 μl or 10 μl of human serum. A buffer solution adapted for immune reactions (a 10 mM phosphate buffer solution of pH 7.0 containing 0.1% BSA, 0.1M sodium chloride and 0.1% sodium azide) was added to make up to a total volume of 300 μl and the contents were mixed well.

The antibody-coupled ball prepared in the above (b) was added to each test tube and the tube was shaken and warmed at 30° C. for 1–4 hours. After the reaction, the reaction solution in each test tube was sucked off and the ball was washed twice with 2–3 ml of a washing solution (a 10 mM phosphate buffer solution of pH 7.0 containing 0.1M sodium chloride) while sucking off the washing solution.

The balls were transferred to other test tubes and 300 μl (500,000 cpm) of [$^{125}$I]-anti-hPH antibody solution was added to each tube and allowed to stand at 4° C. overnight.

The radioactive element-labeled antibody solution was sucked off and the balls were washed twice with 2 ml of a washing solution and the amount of radioactivity of the ball was measured using a γ-counter (5 minutes).

A standard curve was made (see FIG. 1) to read the PH levels in serum therefrom.

(d) Levels of hPH in sera

Using the hPH standard curve shown in FIG. 1, sera from healthy human subjects and patients diagnosed by biopsy as having liver cirrhosis were measured for hPH levels. The results are shown in Table 2.

Values of 30, 68 and 34 ng/ml were obtained for the healthy human subjects while 165, 210 and 940 ng/ml for the patients with liver cirrhosis.

The analytical precision was found to further increase when the labeled polyclonal antibody purified with a hPH-coupled 4B affinity column or its $F(ab')_2$ was used.

TABLE 2

| Samples for assay | | Average counts | | hPH level ng/ml |
|---|---|---|---|---|
| | | CPM | CPM-blank value | |
| Blank (PH: 0 ng) | | 1,657 | — | — |
| Serum samples | | | | |
| Healthy subject | 1 | 1,787 | 130 | 30 |
| Healthy subject | 2 | 1,905 | 248 | 68 |
| Healthy subject | 3 | 1,804 | 147 | 34 |
| Patient with liver cirrhosis | 1 | 2,042 | 385 | 145 |
| Patient with liver cirrhosis | 2 | 2,083 | 426 | 210 |
| Patient with liver cirrhosis | 3 | 2,792 | 1,135 | 940 |

It is understood that the preceding representative examples may be varied within the scope of the present invention, both as to the reagents and immunoassay conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A method for detecting hepatic diseases which are associated with fibrosis by determining the level of human prolyl hydroxylase in a serum sample which comprises:
   (a) contacting a serum sample of a patient suspected of having said hepatic disease associated with fibrosis with a monoclonal antibody specific to the $\beta$-subunit of human prolyl hydroxylase to form an antigen antibody complex bound on a solid support;
   (b) contacting said antigen antibody complex bound on said solid support with a radio-labeled monoclonal or radio-labeled polyclonal antibody specific to human prolyl hydroxylase to form an antibody antigen radio-labeled antibody complex; and
   (c) measuring the amount of radioactivity of said bound antibody antigen radio-labeled antibody complex to determine the level of human prolyl hydroxylase present in said serum sample and wherein a determination of a level of human prolyl hydroxylase higher than normal is indicative of hepatic disease.

2. The method according to claim 1 wherein said hepatic disease is cirrhosis.

* * * * *